United States Patent
Chidsey et al.

(10) Patent No.: US 8,592,565 B2
(45) Date of Patent: Nov. 26, 2013

(54) PREPARATION OF AZIDE-MODIFIED CARBON SURFACES FOR COUPLING TO VARIOUS SPECIES

(75) Inventors: Christopher E. D. Chidsey, San Francisco, CA (US); Anando Devadoss, Palo Alto, CA (US); Neal K. Devaraj, Lawndale, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1857 days.

(21) Appl. No.: 12/008,401

(22) Filed: Jan. 10, 2008

(65) Prior Publication Data

US 2011/0184196 A1 Jul. 28, 2011

Related U.S. Application Data

(60) Provisional application No. 60/880,249, filed on Jan. 12, 2007, provisional application No. 60/920,728, filed on Mar. 29, 2007.

(51) Int. Cl.
| | |
|---|---|
| *C09B 29/00* | (2006.01) |
| *C07C 245/00* | (2006.01) |
| *C07C 321/00* | (2006.01) |
| *C07C 209/00* | (2006.01) |
| *C07C 247/00* | (2006.01) |
| *C09B 27/00* | (2006.01) |
| *C09B 37/00* | (2006.01) |

(52) U.S. Cl.
USPC .............. 534/885; 552/1; 552/8; 534/553; 534/559; 534/565; 534/573; 534/838; 534/850; 564/411; 977/748

(58) Field of Classification Search
USPC .......... 552/1, 8; 534/885, 553, 559, 565, 573, 534/838, 850; 564/411; 977/748
See application file for complete search history.

(56) References Cited

U.S. PATENT DOCUMENTS

| | | | |
|---|---|---|---|
| 5,554,739 | A | 9/1996 | Belmont |
| 5,852,127 | A | 12/1998 | Belfort et al. |
| 2005/0038032 | A1 | 2/2005 | Allison et al. |

FOREIGN PATENT DOCUMENTS

| | | | |
|---|---|---|---|
| JP | 62112662 A | * | 11/1985 |
| JP | 62112662 A | * | 11/1985 |
| WO | WO-03082968 | | 10/2003 |

OTHER PUBLICATIONS

Zhdankin et al., Functionalization of C60 fullerene by hypervalent iodine reagents; Mar. 26-30, 2000; American Chemical Society; Book of Abstracts, 219 ACS National Meeting, ORGN-565.*
Napolitano et al., Addition of iodine azide to allylic alcohols, 1992, Gazzetta Chimica Italiana; 122(6): 233-235.*
Zhdankin et al., "Functionalization of C60 fullerene by hypervalent iodine reagents,"; Mar. 26-30, 2000; American Chemical Society; Book of Abstracts, 219 ACS National Meeting, ORGN-565.*
Fowler et al., "Stereospecific Introduction of Azide Functions into Organic Molecules," J. Am. Chem. Soc., 1967, 89(9): 2077-2082.*

(Continued)

*Primary Examiner* — Jane C Osweckí
(74) *Attorney, Agent, or Firm* — Ropes & Gray LLP (57) ABSTRACT

The invention relates to carbon surfaces modified with one or more azide groups. The invention also relates to methods of modifying carbon surfaces with one or more azide groups.

5 Claims, 10 Drawing Sheets

(56) References Cited

OTHER PUBLICATIONS

Abramovitch, R.A. et al., "Intramolecular Cyclizations of Diphenyl Ether, Benzophenone, and Related 2-Sulfonylnitrenes," J. Org. Chem., 43(6):1218-1226 (1978).

Aichaoui, H. et al., "Unequivocal Preparation of 4- and 5-Acyl-2-aminophenols," Synthesis, 8:679-680 (1990).

Bräse, S. et al., "Organic Azides: An Exploding Diversity of a Unique Class of Compounds," Angew. Chem. Int. Ed., 44(33):5188-5240 (2005).

Collman, J.P. et al., "'Clicking' Functionality onto Electrode Surfaces," Langmuir, 20(4):1051-1053 (2004).

Collman, J.P. et al., "Mixed Azide-Terminated Monolayers: A Platform for Modifying Electrode Surfaces," Langmuir, 22(6):2457-2464 (2006).

Devadoss, A. et al., "Azide-Modified Graphitic Surfaces for Covalent Attachment of Alkyne-Terminated Molecules by 'Click' Chemistry," J. Am. Chem. Soc., 129(17):5370-5371 (2007).

Fischer, W. et al., "The Reaction of Amine Anions with p-Toluenesulfonyl Azide. A Novel Azide Synthesis," J. Am. Chem. Soc., 89(20):5284-5285 (1967).

Fowler, F. W., "Stereospecific Introduction of Azide Functions into Organic Molecules," J. Am. Chem. Soc., 89(9):2077-2082 (1967).

Lahaye, Jacques, "The chemistry of carbon surfaces," Fuel, 77(6):543-547 (1998).

Minisci, F. et al., "Reactivity of Hydroxy and Alkoxy Radicals in Presence of Olefins and Oxidation-Reduction Systems. Introduction of Azido, Chloro and Acyloxy Groups in Allylic Position and Azido-Chlorination of Olefins," Tetrahedron Letters No. 6, 357-360 (1963).

Toda, M. et al., "Biodiesel made with sugar catalyst," Green Chemistry, 438(7065):178 (2005).

* cited by examiner

PREPARATION OF AZIDE-MODIFIED CARBON SURFACES FOR COUPLING TO VARIOUS SPECIES

RELATED APPLICATIONS

This application claims the benefit of priority to U.S. Provisional Patent Application No. 60/880,249, filed Jan. 12, 2007, and U.S. Provisional Patent Application No. 60/920,728, filed Mar. 29, 2007, which applications are hereby incorporated by reference in their entirety.

BACKGROUND

Carbon materials are used in a wide variety of industries and products. These carbon materials include, for example, graphite powder, graphite fibers, carbon fibers, carbon cloth, vitreous carbon products, and activated carbon products. Many of the uses of these carbon materials are discussed below.

Graphite powder, in addition to its use as "lead" in pencils, has many uses in a variety of fields, including electrical, chemical, metallurgical and rocket components. Electrodes formed from graphite are used in steel-making furnaces and in the electrolytic production of chlorine, chlorates, magnesium, and sodium. Graphite is also used to make metallurgical molds and crucibles and chemical reaction vessels. In the field of rockets, graphite is used to make rocket motor nozzles and missile nose cones.

Graphite fibers and carbon fibers are similarly used in a variety of applications. Short or chopped fibers are often used as reinforcement in injection moldings, as well as in automotive brakes, where their good abrasion resistance is desired. High-performance graphite or carbon fibers are used in structural composites, particularly composites utilized by the aerospace field. These fibers also see widespread use in sporting goods such as fishing rods, golf clubs, and tennis rackets.

Carbon cloth or mats are simply textile products formed from long fibers of carbon or graphite. They are useful in areas such as electrostatic dissipation in carpets or computer-related furniture, electromagnetic shielding, and electrostatic painting of sheet-molded automotive parts. The low thermal conductivity also finds uses the field of rocket components.

Vitreous carbon is used in the manufacture of electrical goods such as electrodes and mechanical goods such as crucibles.

Activated carbon exhibits excellent adsorption properties and is therefore used to improve the color of manufactured chemicals, oils, and fats, to control the color, odor, and taste of water, beverages, and food. These gas-adsorbent carbons are also useful in gas separation processes, the recovery of solvent vapors, air conditioning systems, and gas masks.

Fullerenic structures are carbon compounds that include closed-caged compounds such as fullerenes and nanotubes. One of the first fullerenes discovered was the version containing 60 carbon atoms ($C_{60}$) made up of adjacent carbon pentagon and hexagon rings. Other fullerenes such as $C_{36}$, $C_{70}$, and $C_{90}$ have been observed and analyzed. It has been speculated that fullerenic structures both smaller than and larger than $C_{60}$ exist in, for example, combustion-generated soot.

Much effort has been expended over the last several decades to modify the surface chemistry of carbon materials. While it is possible to deposit physically adsorbed material onto the surface of a carbon material, permanently changing its surface chemistry is substantially more difficult.

PCT Patent Application No. WO 92/13983 describes a process for modifying the surfaces of carbon-containing materials by electrochemical reduction of diazonium salts. The process is reportedly applicable, in particular, to carbon plates and carbon fibers for composite materials. Carbon-containing materials modified by the process are also described. Electrochemical reduction of diazonium salts containing functionalized aryl radicals to covalently modify carbon surfaces is also described in Delmar et al., J. Am. Chem. Soc. 1992, 114, 5883-5884.

According to WO 92/13983, the process for modifying the surface of a carbon-containing material consists of grafting an aromatic group to the surface of this material by electrochemical reduction of a diazonium salt including this aromatic group. The carbon-containing material is placed in contact with a diazonium salt solution in an aprotic solvent and is negatively charged with respect to an anode which is also in contact with the diazonium salt solution. Use of a protic solvent is reported to prevent the electrochemical process from producing the intended product as a result of reducing the diazonium triple bond to yield a hydrazine.

There remains a need for alternative methods to modify the surface chemistry of carbon materials and impart desired properties to carbon materials.

SUMMARY OF INVENTION

The present invention provides carbon surfaces modified with one or more azide groups.

The present invention provides a method of modifying a carbon surface with a phenyl azide group, comprising contacting the carbon surface with a diazonium ion of the phenyl azide.

The present invention provides a method of modifying a carbon surface, comprising modifying the carbon surface with a nitro-bearing group, reducing the nitro-bearing group to an amine-bearing group, and converting the amine-bearing group to an azide-bearing group by a diazo transfer reaction. In certain embodiments, nitro-bearing group is a nitrophenyl group and the subsequent azide-bearing group is a phenyl azide group.

The present invention provides a method of modifying a carbon surface with an azide group, comprising modifying the carbon surface with iodine azide.

The present invention provides a method of further modifying a carbon surface modified with an azide group, comprising reacting the azide with a terminal alkyne such that the two groups undergo a cycloaddition reaction.

DETAILED DESCRIPTION OF THE DRAWINGS

DETAILED DESCRIPTION OF THE INVENTION

In one aspect, the present invention provides carbon surfaces modified with one or more azide groups.

In another aspect, the present invention provides carbon surfaces modified with one or more azide-bearing groups, e.g., azido aromatic groups, such as azidophenyl groups.

In another aspect, the present invention provides carbon surfaces modified with one or more nitro-bearing groups, e.g., nitro aromatic groups, such as nitrophenyl groups.

In yet another aspect, the present invention provides carbon surfaces modified with one or more amine-bearing groups, e.g., amino aromatic groups, such as aminophenyl groups.

In still another aspect, the present invention provides carbon surfaces modified with one or more acetamide-bearing groups, e.g., acetamide-bearing aromatic groups, such as acetamidophenyl groups.

In yet another aspect, the present invention provides carbon surfaces modified with one or more nitro groups.

The present invention provides carbon surfaces modified with one or more amine groups.

The present invention provides a method of modifying a carbon surface with a phenyl azide group, comprising contacting the carbon surface with a diazonium ion of the phenyl azide. This may be accomplished, for example, by the conversion of an amino phenyl azide to the corresponding diazonium phenyl azide. Once the diazonium group is formed, it can be reacted with the carbon surface by chemical or electrochemical methods, thereby forming a linkage between the carbon surface and the phenyl azide.

In certain embodiments wherein the diazonium group is reacted with the carbon surface by electrochemical methods, an electrochemical potential between about −50 and about −250 mV vs Ag/AgCl reference electrode is applied for between about 5 and about 15 seconds to modify the carbon surface with the phenyl azide group. In certain embodiments, an electrochemical potential of −100 mV vs Ag/AgCl reference electrode is applied for 10 seconds to modify the carbon surface with the phenyl azide group.

In certain embodiments wherein the diazonium group is reacted with the carbon surface by chemical methods, various diazonium reaction conditions may be employed, such as neat acid conditions or ionic liquid conditions, as is well known in the art.

In certain embodiments, the amino phenyl azide is 4-azidoaniline.

In certain embodiments, the carbon surface being modified may be carbon black, carbon fiber, carbon plates, carbon cloth, activated carbon, vitreous carbon, charcoal, activated charcoal, graphite powder, graphite fibers, carbon nanotubes, fullerenes, or combinations thereof.

A general discussion of diazonium salts and methods for their preparation is found in Morrison and Boyd, Organic Chemistry, 5th Ed., pp. 973-983, (Allyn and Bacon, Inc. 1987) and March, Advanced Organic Chemistry: Reactions, Mechanisms, and Structures, 4th Ed., (Wiley, 1992). According to this invention, a diazonium salt is an organic compound having a diazonium group. In certain embodiments, the diazonium salt may be prepared prior to reaction with the carbon surface or, more preferably, generated in situ using techniques known in the art.

Preparation of the diazonium salt, as known in the art, may be accomplished, for example, by the reaction of a primary amine with an aqueous solution of nitrous acid. In certain embodiments of the present invention, both the nitrous acid and the diazonium salt are generated in situ. Accordingly, the diazonium salt may be generated by combining a primary amine, a nitrite and an acid. In certain embodiments, the primary amine is 4-azidoaniline. The nitrite may be any metal nitrite, for example lithium nitrite, sodium nitrite, potassium nitrite, zinc nitrite, or any organic nitrite such as for example isoamylnitrite or ethylnitrite. In certain embodiments, the nitrite is sodium nitrite. In certain embodiments, one equivalent of sodium nitrite is used. The acid may be any acid, inorganic or organic, which is effective in the generation of the diazonium salt, such as nitric acid, hydrochloric acid, or sulfuric acid. In certain embodiments, the acid is hydrochloric acid. In certain embodiments, the diazonium formation conditions comprise using an excess of acid, such as between about three and about 100 equivalents of acid. However, since azide groups are sensitive to acid, the diazonium formation conditions in the presence of an azide group typically employ fewer equivalents, such as between about three and about ten equivalents of acid, e.g., about three and about five equivalents of acid. In certain embodiments, three equivalents of hydrochloric acid are used. In certain embodiments, the diazonium ion formation conditions comprise maintaining a temperature between about −10 and about 10° C., particularly, between about 0 and about 4° C. In certain embodiments, the diazonium formation conditions comprise maintaining the temperature at 0° C.

The present invention provides a method of modifying a carbon surface, comprising modifying the carbon surface with a nitro-bearing or acetamide-bearing group, converting the nitro-bearing or acetamide-bearing group to an amine-bearing group, and converting the amine-bearing group to an azide-bearing group by a diazo transfer reaction. In certain embodiments, the carbon surface is modified with the nitro-bearing or acetamide-bearing group by modifying the carbon surface with a nitro-bearing or acetamide-bearing group that is further functionalized with a diazonium ion. In particular, the diazonium functionality can be reacted with the carbon surface by chemical or electrochemical methods, thereby forming a linkage between the carbon surface and the nitro-bearing or acetamide-bearing group.

In certain embodiments wherein the diazonium group is reacted with the carbon surface by electrochemical methods, an electrochemical potential between about −50 and about −250 mV vs Ag/AgCl reference electrode is applied for between about 5 and about 15 seconds to modify the carbon surface with the nitro-bearing or acetamide-bearing group. In certain embodiments, an electrochemical potential of −200 mV vs Ag/AgCl reference electrode is applied for 10 seconds to modify the carbon surface with the nitro-bearing or acetamide-bearing group.

In certain embodiments wherein the diazonium group is reacted with the carbon surface by chemical methods, various diazonium reaction conditions may be employed, such as neat acid conditions or ionic liquid conditions, as is well known in the art.

In certain embodiments, the nitro-bearing group is a nitrophenyl group and the subsequent azide group is a phenyl azide group.

In certain embodiments, the carbon surface being modified may be carbon black, carbon fiber, carbon plates, carbon cloth, activated carbon, vitreous carbon, charcoal, activated charcoal, graphite powder, graphite fibers, carbon nanotubes, fullerenes, or combinations thereof.

In certain embodiments, the nitro-bearing molecule that is further functionalized with a diazonium group is formed from the corresponding nitro-bearing amine molecule according to the general procedure outlined above for the preparation of diazonium salts from amines. In certain embodiments, the nitro-bearing amine molecule is 4-nitroaniline.

The present invention provides a method of modifying a carbon surface, comprising directly modifying the carbon surface with a nitro group, reducing the nitro group to an amine group, and converting the amine group to an azide group (e.g., by a diazo transfer reaction or by the reaction of an intermediate diazonium ion with sodium azide).

In certain embodiments of methods of the invention wherein an amine group is converted to an azide group by a diazo transfer reaction, the reaction is accomplished using triflyl azide in the presence of a copper catalyst, such as $CuSO_4$, as is outlined in Brase, S. et al., *Angew. Chem.*, 2005, 44, 5188 and references therein. In certain embodiments, triflyl azide is prepared from trifluoromethansulfonic anhydride and sodium azide. In certain embodiments of methods of the invention wherein an amine group is converted to an azide group by a diazo transfer reaction, the reaction is accomplished by reacting the amine anion with p-toluenesulfonyl azide, as is outlined in Fischer, W. et al., J. Am. Chem. Soc., 1967, 89, 5284 and references cited therein. In certain embodiments, the amine anion is formed by reaction with an alkylmagnesium halide.

In certain embodiments, the carbon surface being modified may be carbon black, carbon fiber, carbon plates, carbon cloth, activated carbon, vitreous carbon, charcoal, activated charcoal, graphite powder, graphite fibers, carbon nanotubes, or combinations thereof.

The direct nitration of a carbon surface can be accomplished using any method suitable for the nitration of aromatic compounds. Such suitable methods may be found in March, Advanced Organic Chemistry: Reactions, Mechanisms and Structure, 4th Ed., pp. 522-525 (John Wiley & Sons, Inc., 1992), and references cited therein. For example, in certain embodiments, the carbon surface is directly modified with a nitro group by reacting the surface with nitric acid and acetic anhydride, sulfuric acid, or trifluoroacetic anhydride. In certain embodiments, the carbon surface is directly modified with a nitro group by reacting the surface with nitric acid and acetic anhydride.

Methods for the reduction of nitro groups, including aromatic nitro groups, to their corresponding amines may be found in Larock, Comprehensive Organic Transformations, 2nd Ed., pp. 821-827 (John Wiley & Sons, Inc., 1999). In certain embodiments, a nitro group, including an aromatic nitro group, can be reduced to its corresponding amine by reacting an aqueous solution of the nitro-modified carbon surface containing ethanol with sodium carbonate, sodium dithionate, and ethyl viologen dibromide.

An acetamide group can be deacetylated to provide the corresponding amine by treatment with strong acid as in Aichaoui, H. et al. *Synthesis*, 1990, 8, 679. Alternatively, the acetamide may be reduced to the corresponding amine by reacting the amide with lithium borohydride treated in situ with methanol as in Soai, K. et al., J. Org. Chem., 1986, 51, 4000.

The present invention provides a method of modifying a carbon surface with a carbonyl azide group, comprising modifying the carbon surface with a carboxyl-bearing group and converting the carboxyl-bearing group to a carbonyl azide-bearing group through a carbonyl halide intermediate or other active carbonyl species. Method for the conversion of a carboxylic acid to a carbonyl azide is described in U.S. Patent Application 2005038032. In certain embodiments, the carboxyl group is present directly on the carbon surface as is described in Lahaye, J. *Fuel*, 1998, 77, 543.

The present invention provides a method of modifying a carbon surface with a sulfonyl azide group, comprising modifying the carbon surface with a sulfonate-bearing group and converting the sulfonate-bearing group to an sulfonyl azide-bearing group. Method for the conversion of a sulfonic acid to a sulfonyl azide is described in Abramovitch et al., *J. Org. Chem.*, 1978, 43, 1218. In certain embodiments, the sulfonate group is introduced directly to the carbon surface as is described in Toda, M., et al. *Nature*, 2005, 438, 178.

The present invention provides a method of modifying a carbon surface with an azide group comprising modifying the carbon surface with a halogen azide, such as iodine azide ($IN_3$), chlorine azide ($ClN_3$), or bromine azide ($BrN_3$). In certain embodiments, the carbon surface is immersed in a solution of halogen azide in acetonitrile. Without wishing to be bound by theory, it is possible that the azide groups are introduced at the carbon surface presumably via a Hassner-type addition to a double bond, as depicted in Scheme 1. In certain embodiments, the surface modification is conducted at room temperature. In certain embodiments, the surface modification with iodine azide is conducted for between about 10 minutes to about 16 hours, or between about 20 minutes to about 60 minutes. In certain embodiments, after the halogen azide is coupled to the carbon surface, halogen atoms bound to the carbon surface are removed by spontaneous elimination of hydrogen halide. In certain embodiments, after the halogen azide is coupled to the carbon surface, halogen atoms bound to the carbon surface are removed by eliminating hydrogen halide using a base, such as potassium tert-butylate. See, for example, Fowler, F. W. et al., "Stereospecific introduction of azide functions into organic molecules." J. Am. Chem. Soc. (1967), 89(9), 2077-2082. In certain embodiments, the resulting azide-modified carbon surface is substantially free of halogen moieties, wherein substantially free means that the substance in question makes up less than 10%, or less than 5%, or less than 4%, or less than 3%, or less than 2%, or less than 1% as compared to the number of azide groups, e.g., on the surface.

Scheme 1

In certain embodiments, the halogen azide is iodine azide.

The halogen azide can be prepared using any suitable method, as are well-known in the art. For example, iodine azide can be prepared by reacting sodium azide and iodine monochloride at 0° C. in a polar, organic solvent. In certain embodiments, the solvent is acetonitrile.

The present invention provides a method of modifying a carbon surface with an azide group comprising contacting the carbon surface with sodium azide in the presence of hydrogen peroxide, ferrous sulphate, and ferric halide (e.g., $FeCl_2$ or $FeBr_2$) or copper halide (e.g., CuCl or CuBr) such that a plurality of azide and halogen moieties are attached to the surface. See, for example, Minisci, F. et al. "Reactivity of hydroxy and alkoxy radicals in presence of olefins and oxidation-reduction systems. Introduction of azido, chloro and acyloxy groups in allylic position and azido-chlorination of olefins." Tetrahedron Lett. (1963), 4, 357-360. In certain embodiments, the carbon surface is immersed in a mixture of alcohol and water (e.g., $EtOH/H_2O$, $iPrOH/H_2O$, or $MeOH/H_2O$). In certain embodiments, after the halogen and the azide are coupled to the carbon surface, the halogen is removed by spontaneous elimination of hydrogen halide. In certain embodiments, after the halogen and the azide are coupled to the carbon surface, the halogen is removed by eliminating hydrogen halide using a base, such as potassium tert-butylate. See, for example, Fowler, F. W. et al., "Stereospecific introduction of azide functions into organic molecules." J. Am. Chem. Soc. (1967), 89(9), 2077-2082. In certain embodiments, the resulting azide-modified carbon surface is substantially free of halogen moieties, wherein substantially free means that the substance in question makes up less than 10%, or less than 5%, or less than 4%, or less than 3%, or less than 2%, or less than 1% as compared to the number of azide groups, e.g., on the surface.

In certain embodiments, the carbon surface being modified may be carbon black, carbon fiber, carbon plates, carbon cloth, activated carbon, vitreous carbon, charcoal, activated charcoal, graphite powder, graphite fibers, carbon nanotubes, or combinations thereof.

Once present, a carbon surface azide group can be used to couple various species to the carbon surface, taking advantage of numerous useful and highly selective coupling reactions of azides. The initial presence of azide on surfaces and the absence of azide after a coupling reaction can be monitored by relatively simple surface analysis techniques such as X-ray photoelectron spectroscopy or infrared spectroscopy. These spectroscopic methods allow for the quantification of the coupling reactions on the carbon surface.

The present invention provides a method of further modifying a carbon surface modified with azide group, comprising reacting the azide with a terminal alkyne under conditions that permit the two groups to undergo a cycloaddition reaction. The cycloaddition of alkynes and azides forms a 1,4-disubstituted 1,2,3-triazole ring. In certain embodiments, the cycloaddition reaction is performed in solution phase, in aqueous or non-aqueous reaction conditions, or the terminal alkyne and associated reagents are presented to the carbon surface in gas phase. This cycloaddition reaction is robust, and can withstand a wide variety of conditions, such as a range of acid conditions (e.g., non-acidic, weakly acidic, strongly acidic), oxidative conditions, and mechanical conditions, such as ultrasonication.

In certain embodiments, the further modification of a carbon surface modified with an azide group is accomplished by coupling to an alkyne-terminated molecule via a Cu(I)-catalyzed Huisgen 1,3-dipolar cycloaddition reaction, popularly known as a "click" reaction, as described in Collman, J. P. et al. Langmuir, 2006, 22, 2457 and references therein. In certain embodiments, the cycloaddition reaction is performed in a mixed aqueous-organic solvent system, such as water/ethanol or dimethyl sulfoxide/water. In certain embodiments, the cycloaddition reaction is performed in a dimethyl sulfoxide/water solvent system in a ratio between about 1:1 and about 5:1, such as about 3:1. In certain embodiments, the active Cu(I) species is generated by reacting 0.01 equivalents of $CuSO_4.5H_2O$ and 0.015 equivalents of sodium ascorbate, 20 equivalents of Cu(II)(tris-(benzyltriazolylmethyl)amine) $(NO_3)_2$ and 400 equivalents of ascorbic acid, or 20-400 equivalents of Cu(I)tris(benzyltriazolylmethyl)amine tetrafluoroboride and 400-8000 equivalents of hydroquinone as compared to acetylene species. In certain embodiments, the active Cu(I) species is generated by reacting 20 equivalents of Cu(II)(tris-(benzyltriazolylmethyl)amine)$(NO_3)_2$ and 400 equivalents of ascorbic acid as compared to acetylene species. In certain embodiments, the reaction time is between about five minutes and about 15 hours, such as between about 15 minutes and about six hours. In certain embodiments, the reaction time is about one hour.

The modified carbon surfaces of this invention may be used in the same types of applications as the corresponding unmodified carbon surfaces. The azide groups attached to the carbon surface, however, can be used to modify and improve the properties of a given carbon surface for a particular use. The azide groups may be used to introduce various functional molecules to the carbon surface, such as electrocatalysts for fuel cell applications, polymers for coating the carbon fiber surfaces, proteins, nucleic acids, or ligands for biological assays, and the like. Coupling of such molecules to the modified carbon surface may be accomplished, for example, as is described above for the cycloaddition reaction of the azide group with a terminal alkyne. Advantages of the cycloaddition reaction described above may include the reduced side product formation, quantitative reaction yield, and ease of monitoring reaction progress, e.g., using relatively simple surface spectroscopy techniques.

In certain embodiments, the reactions employed to modify the carbon surfaces as described herein, may result in the introduction of multiple groups to the carbon surface. For example, the method of modifying a carbon surface with an azide group comprising modifying the carbon surface with a halogen azide may result in the introduction of multiple azide groups on the carbon surface. The introduction of multiple groups to a carbon surface is fully contemplated by the present invention.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "alkylamino", as used herein, refers to an amino group substituted with at least one alkyl group.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "halo" and "halogen" as used herein means halogen and includes chloro, fluoro, bromo, and iodo.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Unless specifically stated as "unsubstituted," references to chemical moieties herein are understood to include substituted variants. For example, reference to an "aryl" group or moiety implicitly includes both substituted and unsubstituted variants.

EXAMPLES

Example 1

Modification of a Carbon Surface with an Azide Functionality Using Iodine Azide as Reagent Preparation of Graphitic Surfaces:

Pyrolyzed photoresist films (PPF) were used as graphitic surfaces. PPF samples were prepared using reported methods. Briefly, the photoresist AZ4990 was spin coated (6000 rpm, 30 s) onto a clean Si wafer. Three such coatings were applied and between each coating the wafers were baked at 110° C. for 1 min. The photoresist coated wafers were cut into approximately 2×2 cm$^2$ pieces and placed in a tube furnace. The samples were pyrolyzed in the furnace at 1000° C. for 1 hr 30 mins and then allowed to cool down to room temperature in forming gas atmosphere (flow rate=4 Lmin$^{-1}$). After reaching room temperature, the samples were removed from the furnace and stored in vacuum until used. The thickness of the graphitic film was found to be around 1.6 μm using a profilometer. The sheet resistance was found to be around 30 Ω/square using a four-point probe. This corresponds to a film resistivity of around 5 mΩcm.

Edge plane graphite surfaces were obtained by polishing the sides of a thick block of HOPG sample. After polishing using sand paper and then on a silicon carbide paper, the samples were sonicated in chloroform and acetonitrile for 10 s each to remove any loosely attached carbon particles.

Preparation of Iodine Azide Solution:

Iodine azide was prepared in situ from sodium azide and iodine monochloride according to the literature method. Briefly, a glass beaker containing 0.02 g of sodium azide in 10 ml of acetonitrile was stirred and allowed to attain 0° C. in an ice bath. 5 μL of iodine monochloride (corresponding to a final concentration of 10 mM of iodine azide in acetonitrile) was added to the sodium azide solution under vigorous stirring. An immediate appearance of brownish yellow color corresponded to the formation of iodine azide. The solution was allowed to stand at 0° C. with stirring for 15 mins after which the solution was warmed to room temperature prior to use.

Preparation of Azide Modified Carbon Surfaces:

PPF samples stored in vacuum were sonicated in acetone, chloroform and isopropanol in that order for approximately 20 s to remove any loosely attached carbon particles on the surface. The clean PPF samples were immersed in 10 mM iodine azide solution for 60 minutes. After surface modification the samples were washed with acetonitrile and chloroform to remove any physically adsorbed iodine azide molecules. The surfaces were then blow dried with nitrogen and stored in vacuum.

The surface coverage of the azide groups was determined to be $4.4 \pm 1.3 \times 10^{13}$ moieties/cm$^2$ for an immersion time of 20 mins. Extending the immersion time to 60 mins gave an azide surface coverage of $7.3 \pm 1.4 \times 10^{13}$ moieties/cm$^2$. Further increase up to 16 h did not show any significant increase in the surface coverage. During the course of iodine azide treatment and subsequent reactions the surface coverage of oxygen remained at the value obtained after pyrolysis of the photoresist, around $2.2 \times 10^{14}$ atoms/cm$^2$.

Figure 1A:
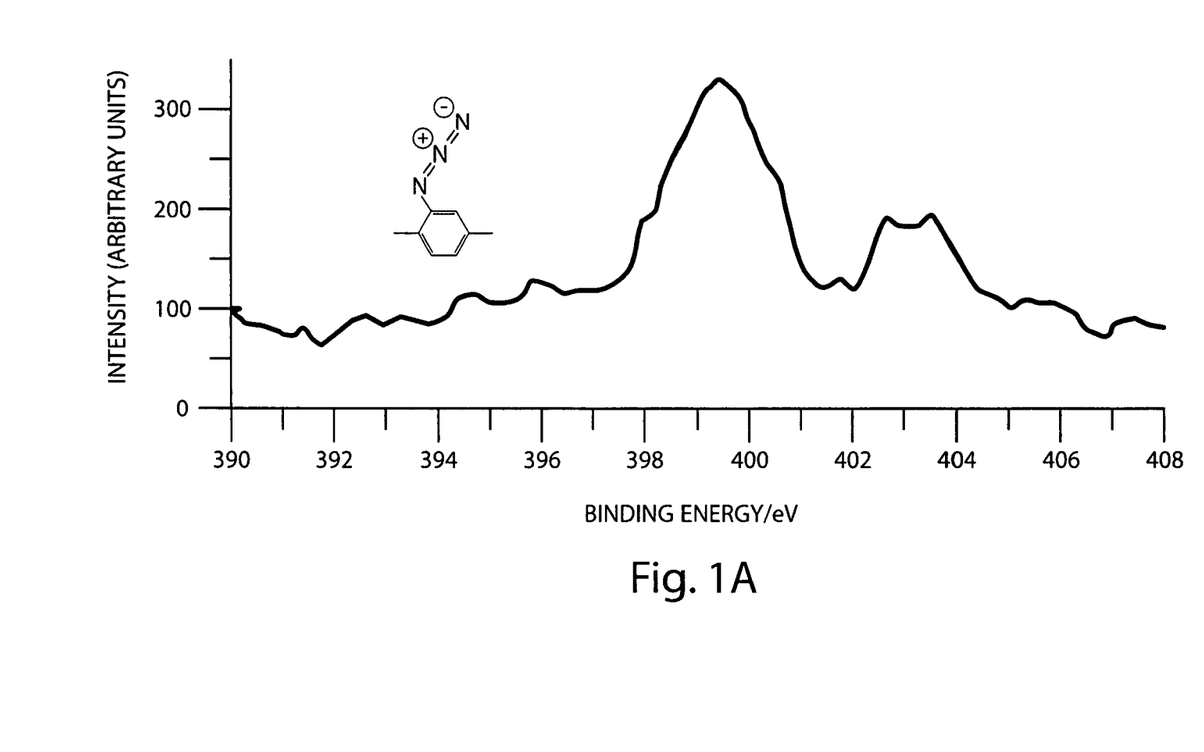
FIG. 1 shows the N 1s X-ray photoelectron spectra obtained at an azide-modified graphitic surface (a) before and (b) after reaction with ethynylferrocene. The inset of FIG. 1(b) shows a cyclic voltammogram obtained at 5 V/s after attachment of ethynylferrocene.

FIG. 1a shows the X-ray photoelectron spectroscopy (XPS) N 1s data obtained at an iodine azide-treated surface. There are peaks at 399 eV and 403 eV with a peak area ratio of 2:1 as expected for azide groups on the surface. Peaks due to iodine atoms corresponding to only 10% of the surface coverage of azides were also observed. These observations suggest that addition of iodine azide to the double bonds at the graphene sheets is followed by a spontaneous elimination of hydrogen iodide to form aromatic azides. An S-Probe Monochromatized XPS Spectrometer (Surface Science Instruments) was used for XPS analysis. Al(Kα) radiation (1486 eV) was used as the probe. The angle between the sample surface and the analyzer was 35°. Analysis of the spectra was done using the software available with the instrument.

Example 2

Modification of a Carbon Surface with a Phenyl Azide Using 4-Azidoaniline as Starting Reagent An aqueous solution containing 1 mM 4-azidoaniline, 100 mM potassium chloride, and 3 mM hydrochloric acid was purged with nitrogen and stirred in an ice bath (preferably in a temperature range of 0-4° C.). To the azidoaniline solution was added 25 μl of 1 M sodium nitrite in water to form the diazonium ions. The mixture was stirred with nitrogen purging for 15 minutes in the ice bath. The ice cold solution was transferred to an electrochemical cell with carbon surface as working electrode. An electrochemical potential of −100 mV vs Ag/AgCl reference electrode was applied for 10 seconds to modify the carbon surface with phenyl azide groups. (Varying the potential and time can permit control of the surface coverage.) The carbon surface was removed from the electrochemical cell and washed with water and acetone and stored in dark.

Example 3

Modification of a Carbon Surface with an Azide Functionality Using 4-Nitroaniline as Starting Reagent An aqueous solution containing 1 mM 4-nitroaniline, 100 mM potassium chloride, and 3 mM hydrochloric acid was purged with nitrogen and stirred in an ice bath (preferred temperature range of 0-4° C.). An aqueous solution of sodium nitrite was added, so that the final concentration was 1.5 mM, to the nitroaniline solution to form the diazonium ions. The mixture was stirred with nitrogen purging for 15 minutes in the ice bath. The ice cold solution was transferred to an electrochemical cell with carbon surface as working electrode. An electrochemical potential of −200 mV vs Ag/AgCl reference electrode was applied for 10 seconds to modify the carbon surface with nitro phenyl groups. The carbon surface was removed from the electrochemical cell and washed with water and acetone. The nitrophenyl-modified carbon surface was immersed in a nitrogen purged, aqueous solution containing 16% ethanol (v/v), 0.5 M sodium carbonate, 0.5 M sodium dithionite and 6 mg of ethyl viologen dibromide for 10 hours to reduce the nitro groups to amine groups. The amine-modified surface was washed with water and acetone.

The amine modified surface is immersed in an ice cold aqueous solution containing 100 mM hydrochloric acid and an aqueous solution of sodium nitrite is added dropwise until the final concentration of sodium nitrite is 1 mM. The sample is left for 15 minutes in an ice bath to form diazonium ions on the surface. An aqueous solution of sodium azide is added to the solution such that the final concentration of sodium azide is 3 mM and left for 15 minutes at room temperature to form phenyl azide groups on the surface. The carbon sample is washed and rinsed with water.

Example 4

Modification of a Carbon Surface with an Azide Functionality Using Direct Nitration of the Carbon Surface Carbon sample was immersed in nitrogen purged concentrated nitric acid containing 80% (v/v) acetic anhydride for 4 hours to modify the surface with nitro groups. The nitro modified surface was rinsed with water and was immersed in a nitrogen-purged, aqueous solution containing 16% ethanol (v/v), 0.5 M sodium carbonate, 0.5 M sodium dithionite and 6 mg of ethyl viologen dibromide for 10 hours to reduce the nitro groups to amine groups. The amine-modified surface was washed with water and acetone.

The amine-modified surface is immersed in an ice cold aqueous solution containing 100 mM hydrochloric acid, and an aqueous solution of sodium nitrite is added dropwise until the final concentration of sodium nitrite is 1 mM. The sample is left for 15 minutes in an ice bath to form diazonium ions on the surface. An aqueous solution of sodium azide is added to the solution such that the final concentration of sodium azide is 3 mM and left for 15 minutes at room temperature to form azide groups on the surface. The carbon sample is washed and rinsed with water.

Example 5

Reaction of an Azide-Modified Surface with an Acetylene-Terminated Molecule

Azide-modified PPF samples were immersed in a 3:1 DMSO:H$_2$O solution containing 20 µM of acetylene-terminated molecule, 400 µM of Cu(II)(tris-(benzyltriazolylmethyl)amine)(NO$_3$)$_2$, and 8 mM ascorbic acid for 1 hr. After modifying with ferrocene or trifluoromethyl-benzene, the samples were washed with chloroform and acetone and blow dried with nitrogen.

Figure 1B:
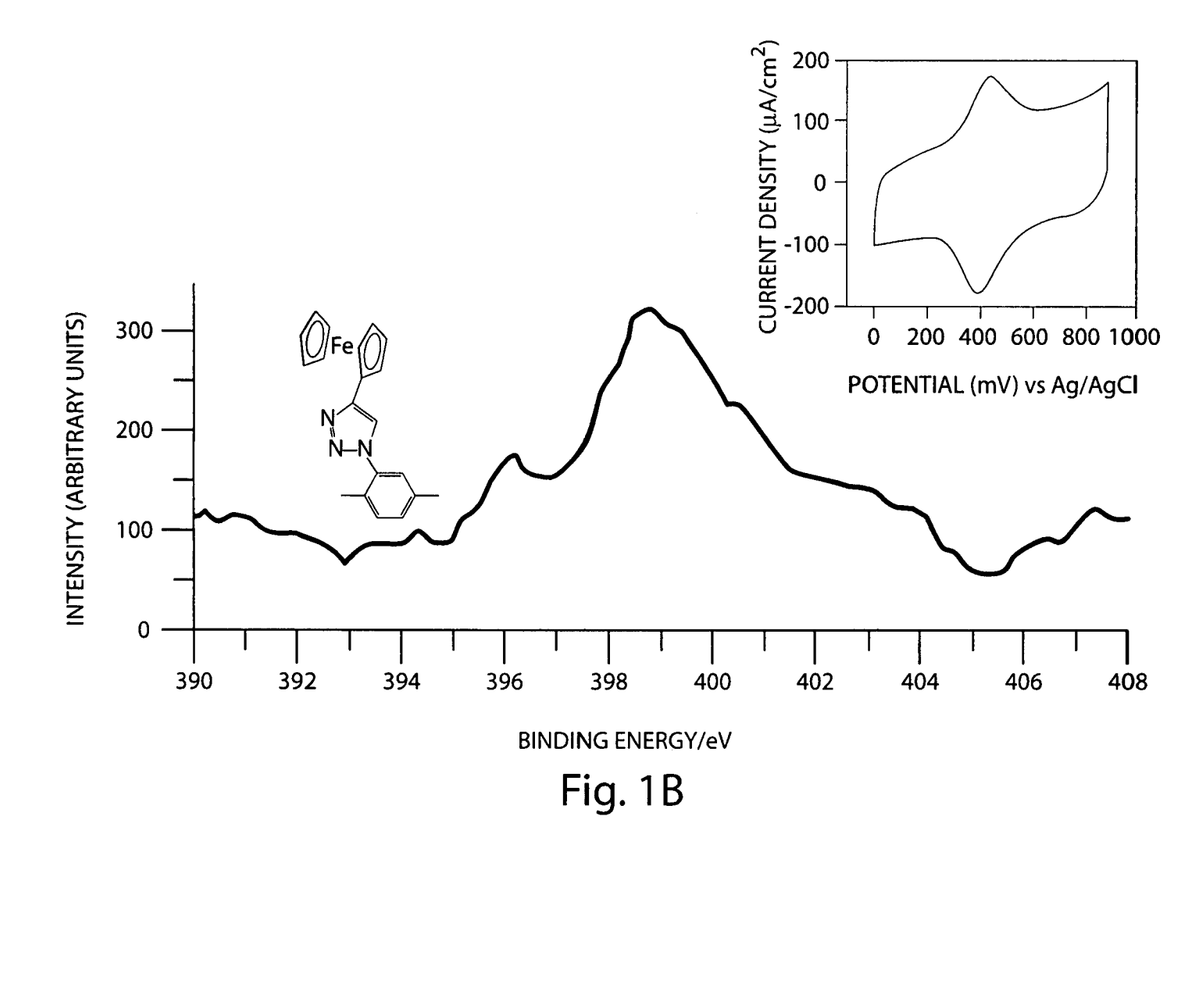
Figure 2:
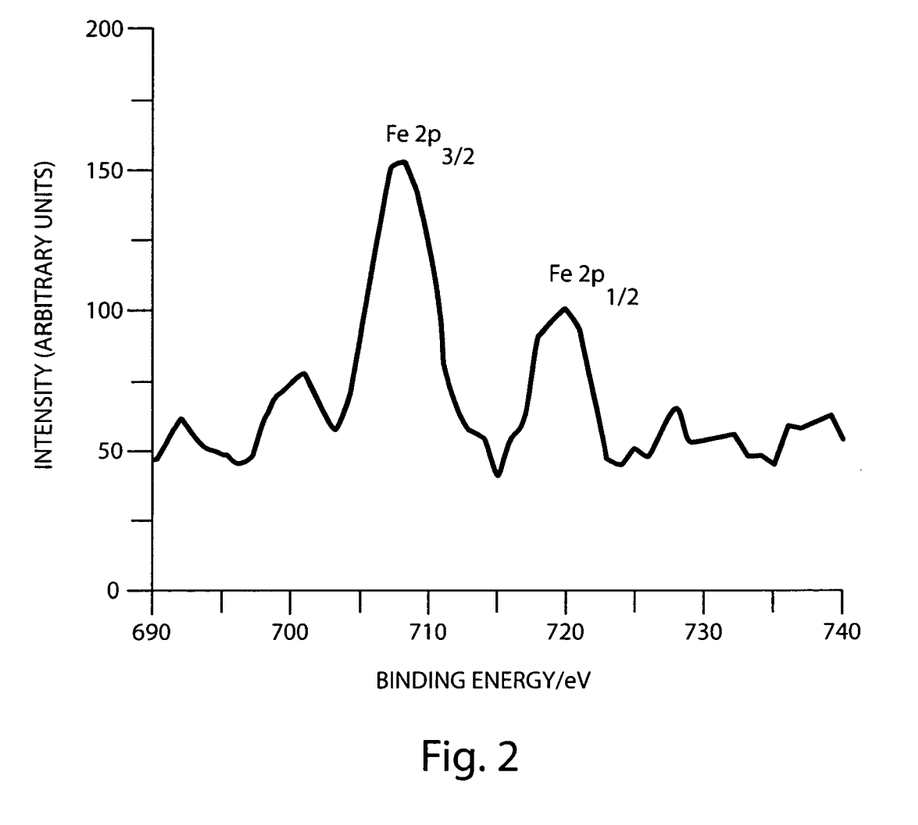
FIG. 2 shows the X-ray photoelectron spectra indicating the presence of iron in an ethynylferrocene coupled surface.

FIG. 1b shows the XPS data obtained at the azide-modified surface after undergoing the cycloaddition reaction with 20 µM ethynylferrocene in 3:1 DMSO:H$_2$O solution containing 400 µM Cu(I)(tris-(benzyltriazolylmethyl)amine)(NO$_3$) as catalyst. The absence of the peak at 403 eV and broadening of the peak at 399 eV is consistent with formation of a 1,2,3 triazole. The area under the broader peak at 399 eV after the cycloaddition reaction is equal to the area under the peaks at 403 and 399 eV before the cycloaddition reaction. These observations suggest that the azide present on the surface forms the 1,2,3 triazole with 100% yield. The presence of ferrocene on the surface was confirmed by the XPS 2p$_{3/2}$ and 2p$_{1/2}$ peaks for iron at 706 and 720 eV in FIG. 2. The azide was stable for several minutes of exposure to the Al Kα radiation. After 10 mins the ratio of the area of the 399 peak to the 403 eV peak decreased to 1:3 from 1:2. Extensive exposure of the X-ray radiation presumably caused liberation of dinitrogen.

The inset of FIG. 1b shows the cyclic voltammetric data obtained at an azide-modified carbon surface coupled with ethynylferrocene in an aqueous solution containing 1 M perchloric acid. A well defined redox peak (E°=0.42 V vs Ag/AgCl) was observed. The peak current was found to vary linearly with scan rate in the range of 1-10 V/s and was consistent with a surface-immobilized ferrocene. The full-width-at-half-maximum of the anodic and cathodic peaks were found to be roughly 0.15 V and approximately 50% greater than the ideal Nernstian width suggesting some heterogeneity or interaction among the ferrocenes. Using the coulombic charge under the reduction and oxidation peaks a surface coverage estimate of 2×10$^{13}$ moieties/cm$^2$ was obtained. These surface coverage values agreed with the values obtained using XPS analysis.

No peaks corresponding to ferrocene redox couple were observed when ethynylferrocene was reacted on an azide-modified graphitic surface in the absence of the Cu(I) catalyst or when a bare graphitic surface was immersed in a solution containing ethynylferrocene.

Edge plane graphite has also been treated with iodine azide and subsequently coupled to ethynylferrocene by a cycloaddition reaction. Higher coverages of up to 1.4×10$^{14}$ moieties/cm$^2$ were obtained. Similar experiments on basal plane of graphite did not show a surface-immobilized ferrocene redox couple. These results support the model of azides being modified at the edges of graphene sheets as shown in Scheme 1.

Figure 3A:
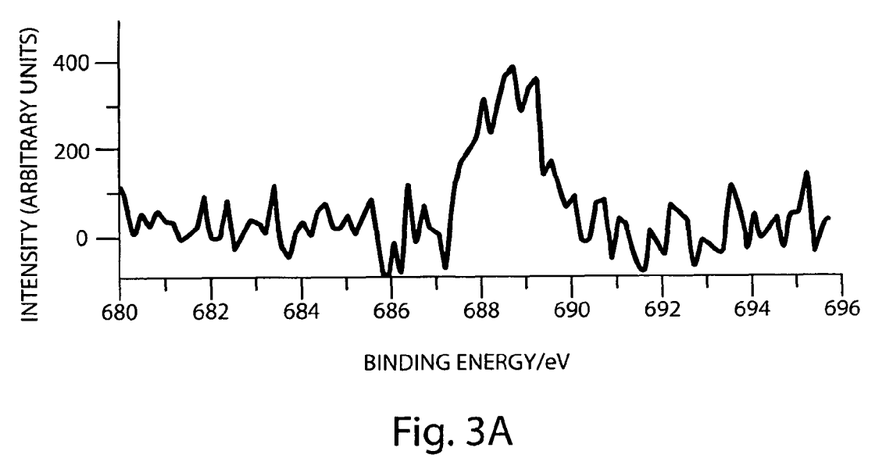
FIG. 3 shows the F is X-ray photoelectron spectra indicating the presence of fluorine peaks (a) before and (b) after treating a trifluoromethyl-benzene-modified surface with 1 M HCl at 55° C. for 60 minutes.
Figure 3B:
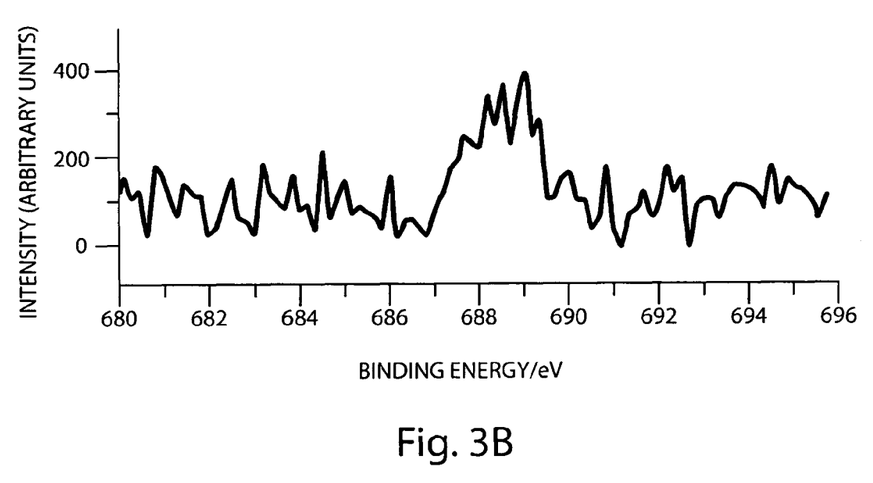
Figure 4:
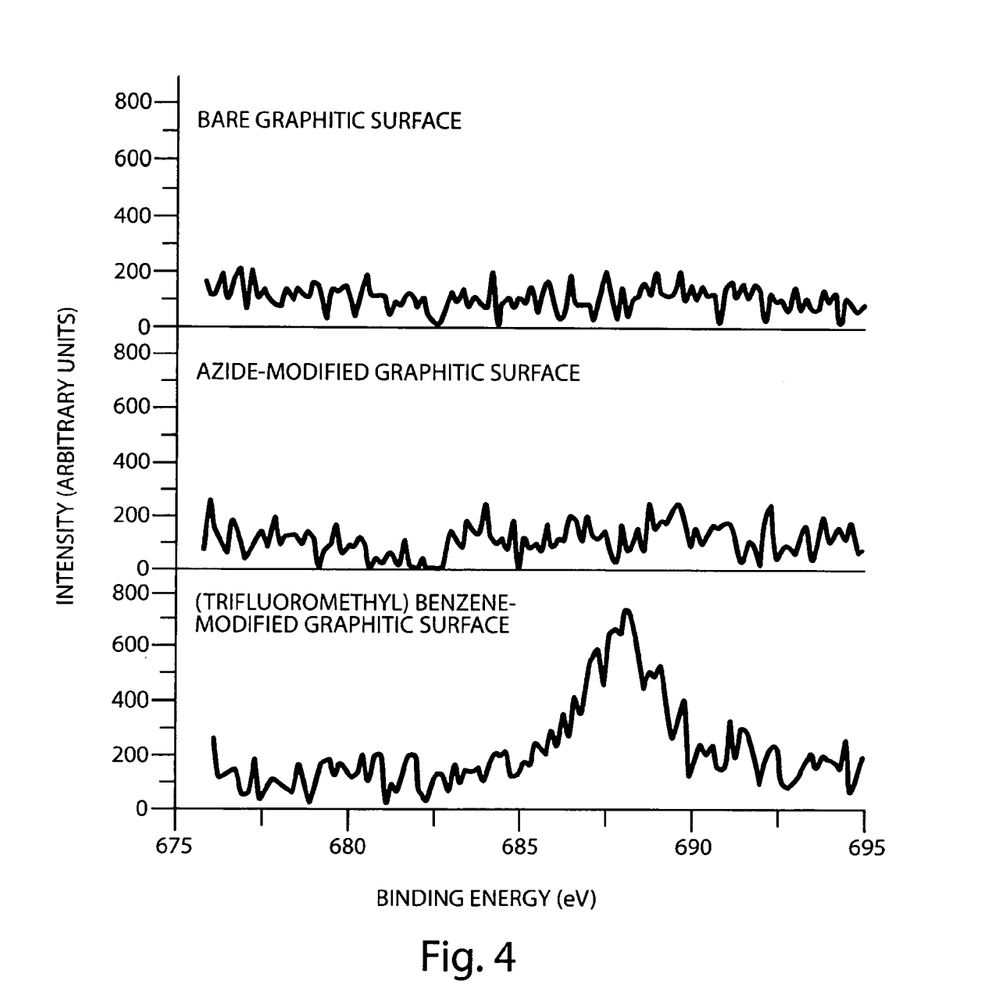
FIG. 4 shows the X-ray photoelectron spectra displaying the fluorine region before and after modifying the graphitic surface with 4-(trifluoromethyl)-benzene.
Figure 5A:
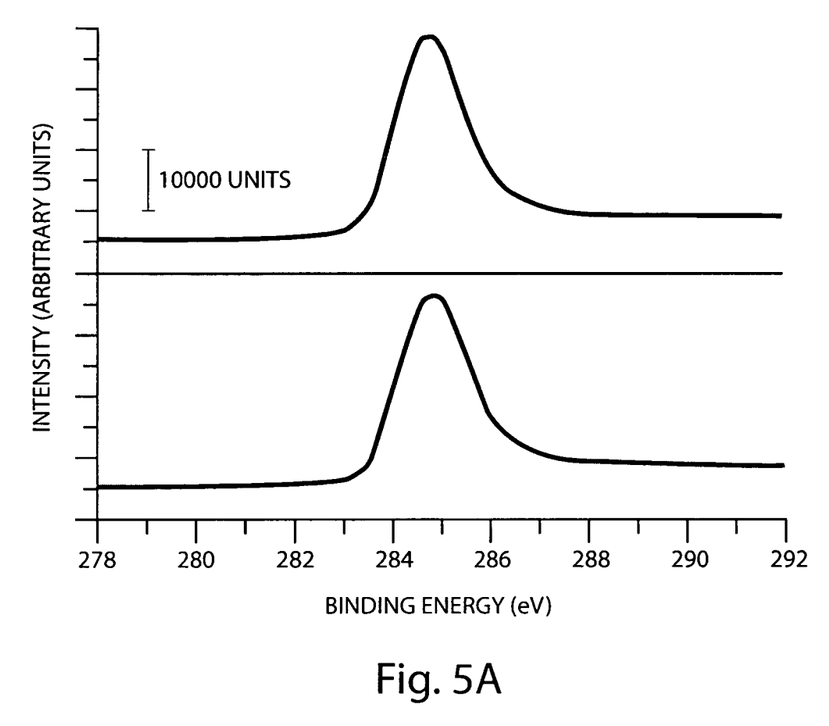
FIG. 5 shows the X-ray photoelectron spectra of the C, N, O, and F regions (a, b, c, and d, respectively) before and after treatment with 1 M HCl.
Figure 5B:
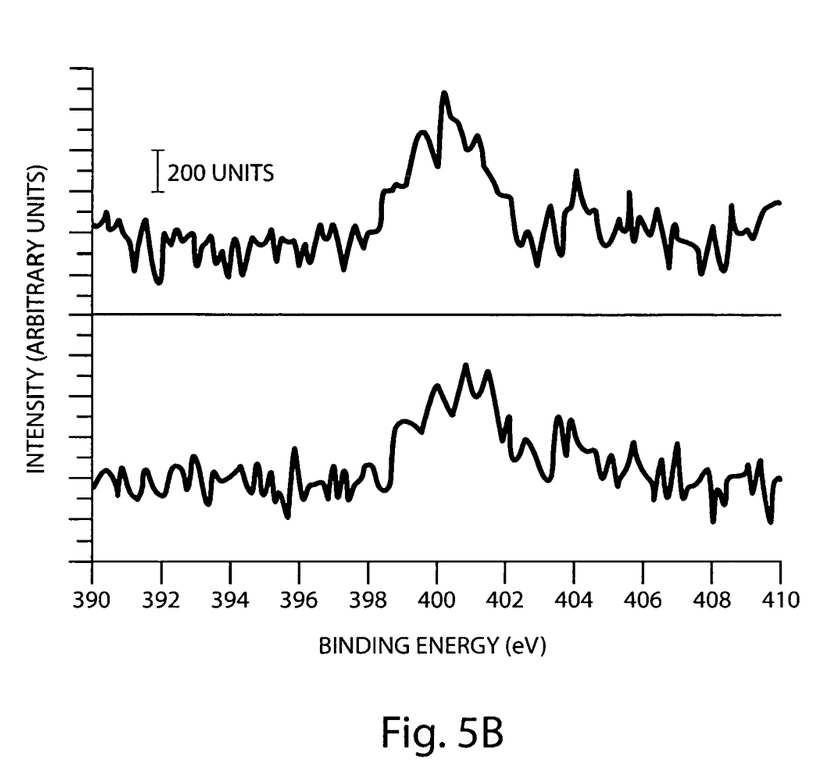
Figure 5C:
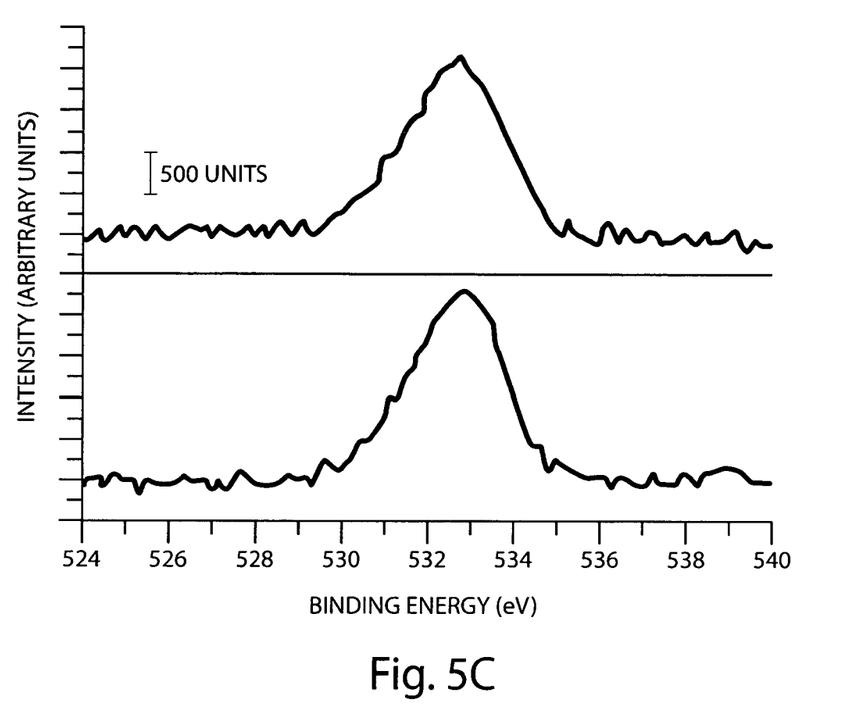
Figure 5D:
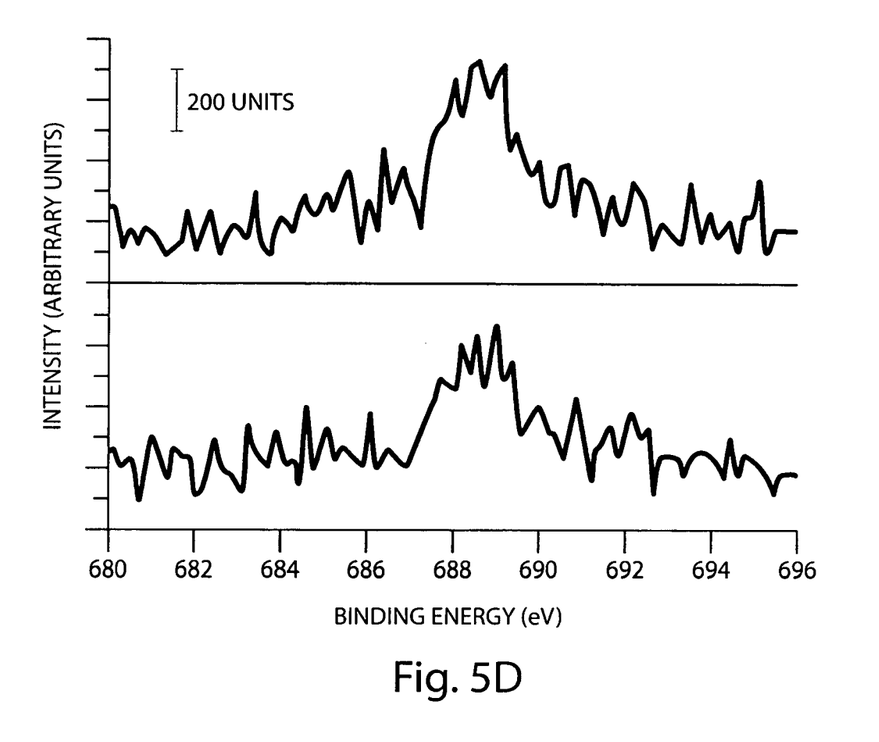

The azide-modified graphitic surfaces were treated with 20 µM of 1-ethynyl-4-(trifluoromethyl)benzene in 3:1 DMSO: H$_2$O solution containing 400 µM Cu(I)(tris-(benzyltriazolylmethyl)amine)(NO$_3$) as catalyst to form a (trifluoromethyl) benzene-modified surface. FIG. 3a shows the peaks due to fluorine atoms present in a (trifluoromethyl)benzene-coupled graphitic surface. A surface coverage of 1.5×10$^{13}$ moieties/cm$^2$ was estimated for the (trifluoromethyl)benzene groups using the XPS peaks of fluorine and carbon, shown in FIG. 4. FIG. 3b shows the fluorine peaks observed at the same surface after an acid hydrolysis treatment (1 M HCl for 60 min at 55° C.). No significant change in fluorine or oxygen surface coverage was observed suggesting the triazole linker is stable to acid hydrolysis.

FIG. 5 shows 4-(trifluoromethyl)benzene-coupled surfaces before and after hydrolysis in 1 M HCl for 60 minutes at 55° C. The XPS spectra of the C region, the N region, the O region, and the F region are shown (a, b, c, and d, respectively). The top spectrum of each region corresponds to the spectrum obtained before hydrolysis, and the bottom spectra were obtained at the same sample after subjecting to the hydrolysis conditions. An analysis of the oxygen peaks showed that the hydrolysis treatment did not alter the oxygen content of the surface. Exposing the 4-(trifluoromethyl)benzene-modified surfaces to air for 10 days did not show any change in fluorine or oxygen content suggesting that these surfaces are stable to air oxidation.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method of modifying a carbon surface with an azide group, comprising contacting the carbon surface with $IN_3$, $ClN_3$, or $BrN_3$, wherein the carbon surface is selected from carbon black, carbon fiber, carbon plates, carbon cloth, activated carbon, vitreous carbon, charcoal, activated charcoal, graphite powder, graphite fibers, carbon nanotubes, fullerenes, or combinations thereof.

2. The method of claim 1, wherein the carbon surface is contacted with $IN_3$.

3. The method of claim 1, further comprising removing iodine chlorine or bromine atoms bound to the carbon surface by elimination of hydrogen iodide, hydrogen chloride or hydrogen bromide.

4. The method of claim 3, wherein the elimination of hydrogen iodide, hydrogen chloride or hydrogen bromide is accomplished using potassium tert-butylate.

5. The method of claim 1, wherein contacting the carbon surface with $IN_3$, $ClN_3$, or $BrN_3$ is performed in acetonitrile at room temperature.

* * * * *